(12) United States Patent
Buckley et al.

(10) Patent No.: US 7,498,399 B2
(45) Date of Patent: Mar. 3, 2009

(54) METHOD OF PREPARING ESTER-SUBSTITUTED DIARYL CARBONATES

(75) Inventors: Paul William Buckley, Scotia, NY (US); David Michael Dardaris, Ballston Spa, NY (US); Patrick Joseph McCloskey, Watervliet, NY (US)

(73) Assignee: Sabic Innovative Plastics IP B.V., Bergen op Zoom (NL)

( * ) Notice: Subject to any disclaimer, the term of this patent is extended or adjusted under 35 U.S.C. 154(b) by 268 days.

(21) Appl. No.: 11/421,359

(22) Filed: May 31, 2006

(65) Prior Publication Data

US 2007/0282091 A1 Dec. 6, 2007

(51) Int. Cl.
*C08G 64/00* (2006.01)
*C08G 63/02* (2006.01)
(52) U.S. Cl. .................. 528/196; 264/176.1; 264/219; 422/131; 502/150; 502/208; 528/86; 528/198; 528/271; 528/272; 558/268; 558/274
(58) Field of Classification Search .............. 264/176.1, 264/219; 528/86, 196, 198, 271, 272; 558/268, 558/274; 422/131; 502/150, 208
See application file for complete search history.

(56) References Cited

U.S. PATENT DOCUMENTS

| 3,470,133 | A | * | 9/1969 | Ohme ........................ 528/490 |
|---|---|---|---|---|
| 4,323,668 | A | | 4/1982 | Brunelle |
| 5,091,591 | A | | 2/1992 | Cipullo |
| 5,151,491 | A | | 9/1992 | Sakashita et al. |
| 5,276,129 | A | | 1/1994 | Sakashita et al. |
| 5,336,750 | A | | 8/1994 | Tuinstra et al. |
| 5,525,701 | A | | 6/1996 | Tominari et al. |
| 5,696,222 | A | | 12/1997 | Kaneko et al. |
| 5,739,258 | A | * | 4/1998 | Zaby et al. .................. 528/198 |
| 6,177,536 | B1 | | 1/2001 | Anamizu et al. |
| 6,252,036 | B1 | | 6/2001 | Hatono et al. |
| 6,300,459 | B1 | | 10/2001 | Kaneko et al. |
| 6,303,734 | B1 | | 10/2001 | Funakoshi et al. |
| 6,399,739 | B1 | | 6/2002 | McCloskey et al. |
| 6,403,754 | B1 | | 6/2002 | McCloskey et al. |
| 6,410,777 | B1 | | 6/2002 | Kaneko et al. |
| 6,417,291 | B1 | | 7/2002 | Kaneko et al. |
| 6,420,512 | B1 | | 7/2002 | McCloskey et al. |
| 6,420,588 | B1 | | 7/2002 | McCloskey et al. |
| 6,469,192 | B1 | | 10/2002 | Burnell et al. |
| 6,500,914 | B1 | | 12/2002 | Brack et al. |
| 6,506,871 | B1 | | 1/2003 | Silvi et al. |
| 6,518,391 | B1 | | 2/2003 | McCloskey et al. |
| 6,525,163 | B1 | | 2/2003 | Brack et al. |
| 6,548,623 | B2 | | 4/2003 | Brunelle et al. |
| 6,590,068 | B2 | | 7/2003 | Brack et al. |
| 6,600,004 | B1 | | 7/2003 | McCloskey et al. |
| 6,653,434 | B2 | | 11/2003 | Brack et al. |
| 6,706,846 | B2 | | 3/2004 | Brack et al. |
| 6,710,156 | B2 | | 3/2004 | Whitney et al. |
| 6,723,823 | B2 | | 4/2004 | McCloskey et al. |
| 6,734,277 | B2 | | 5/2004 | Brack et al. |
| 6,747,119 | B2 | | 6/2004 | Brack et al. |
| 6,790,929 | B2 | * | 9/2004 | Silvi et al. .................. 528/198 |
| 2002/0132957 | A1 | | 9/2002 | Brack et al. |
| 2003/0060649 | A1 | | 3/2003 | burnell et al. |
| 2004/0068086 | A1 | | 4/2004 | Day et al. |
| 2004/0087756 | A1 | | 5/2004 | Ramesh et al. |
| 2005/0234211 | A1 | | 10/2005 | Martinez et al. |
| 2006/0025622 | A1 | | 2/2006 | Buckley et al. |
| 2006/0069228 | A1 | | 3/2006 | McCloskey et al. |

FOREIGN PATENT DOCUMENTS

| EP | 0980861 | 2/2000 |
|---|---|---|
| JP | 5009282 | 1/1993 |
| JP | 10-101786 | 4/1998 |
| JP | 10-101787 | 4/1998 |
| JP | 11-302228 | 11/1999 |
| JP | 2000128976 A | 5/2000 |
| JP | 2000129112 | 5/2000 |
| JP | 2002309015 | 10/2002 |
| WO | 03040208 | 5/2003 |
| WO | 03106149 | 12/2003 |
| WO | 2006049987 A1 | 5/2006 |

* cited by examiner

*Primary Examiner*—Terressa M Boykin
(74) *Attorney, Agent, or Firm*—Larson & Anderson, LLC

(57) ABSTRACT

An improved method for the preparation of ester-substituted diaryl carbonates prepared by reacting phosgene with recycle streams of ester-substituted phenols from reaction processes using a tetraalkyl ammonium hydroxide catalyst, a tetraalkyl phosphonium hydroxide catalyst, or both, where at least one alkyl group of the tetraalkyl ammonium hydroxide or the tetraalkyl phosphonium hydroxide is a methyl group. The improvement includes the step of treating the recycle stream to reduce the concentration of a trialkyl amine, trialkyl phosphine, or both, if present, from the recycle stream prior to reacting it with phosgene to form the ester-substituted diaryl carbonate.

22 Claims, 3 Drawing Sheets

METHOD OF PREPARING ESTER-SUBSTITUTED DIARYL CARBONATES

BACKGROUND

Ester-substituted diaryl carbonates such as bis-methyl salicyl carbonate (BMSC) have proven to be useful starting materials in the preparation of polycarbonates via the melt reaction of a diaryl carbonate with dihydroxy compounds. See for example, U.S. Pat. No. 4,323,668 in which rates of polymerization of bis-methyl salicyl carbonate with bisphenol A were shown to be higher than the corresponding rates of polymerization of bisphenol A with an unsubstituted diaryl carbonate, such as diphenyl carbonate. The product polycarbonate formed using ester-substituted carbonates, such as BMSC, contain high amounts of reaction by-products such as ester-substituted phenols (e.g. methyl salicylate (MS)), inter alia, that are often removed prior to achieving a finished polycarbonate product. In order to achieve high efficiencies and to decrease amounts of unusable waste by-products generated by polycarbonate production facilities, it would be desirable to find a use for the removed by-products. The present invention provides a method of making ester-substituted diaryl carbonates using the by-product ester-substituted phenol.

SUMMARY OF INVENTION

In one embodiment, the present invention provides an improved method for the preparation of ester-substituted diaryl carbonates prepared by reacting phosgene with recycle streams of ester-substituted phenols from reaction processes using a tetraalkyl ammonium hydroxide catalyst, a tetraalkyl phosphonium hydroxide catalyst, or both, where at least one alkyl group of the tetraalkyl ammonium hydroxide or the tetraalkyl phosphonium hydroxide is a methyl group. The improvement comprises the step of treating the recycle stream to reduce the concentration of a trialkyl amine, trialkyl phosphine, or both, if present, from the recycle stream prior to reacting it with phosgene to form the ester-substituted diaryl carbonate.

In another embodiment, the present invention provides an improved method for the manufacture of polycarbonate using as a carbonate source an ester-substituted diaryl carbonate prepared by reacting phosgene with recycle streams of ester-substituted phenol from reaction processes using a tetraalkyl ammonium hydroxide catalyst, a tetraalkyl phosphonium hydroxide catalyst, or both, where at least one alkyl group of the tetraalkyl ammonium hydroxide or the tetraalkyl phosphonium hydroxide is a methyl group. The improvement comprises the step of treating the recycle stream to reduce the concentration of a trialkyl amine, trialkyl phosphine, or both, if present, from the recycle stream prior to reacting it with phosgene to form the ester-substituted diaryl carbonate.

In another embodiment the present invention provides a facility for making polycarbonate. The facility comprises:
(i) a melt polymerization reactor system comprising a reaction vessel containing a reaction mixture, said reaction mixture comprising a dihydroxy compound, an ester-substituted diaryl carbonate, and a catalyst, wherein the catalyst comprises a tetraalkyl ammonium hydroxide, a tetraalkyl phosphonium hydroxide, or both, wherein at least one alkyl group of the tetraalkyl phosphonium hydroxide or the tetraalkyl ammonium hydroxide is a methyl group,
(ii) an ester-substituted diaryl carbonate reactor system comprising a reaction vessel containing an ester-substituted phenol and phosgene,
(iii) a recycle ester-substituted phenol line, connected to both the melt polymerization reactor system and to the ester-substituted diaryl carbonate reactor system, the recycle line containing a recycle stream of an ester-substituted phenol and a catalyst degradation product, wherein the catalyst degradation product comprises a trialkyl amine, a trialkyl phosphine, or both, and
(iv) means for reducing catalyst degradation product concentration in the recycle ester-substituted phenol line, connected to the recycle ester-substituted phenol line between the melt polymerization reactor system to the ester-substituted diaryl carbonate reactor system.

DETAILED DESCRIPTION

Figure 1:
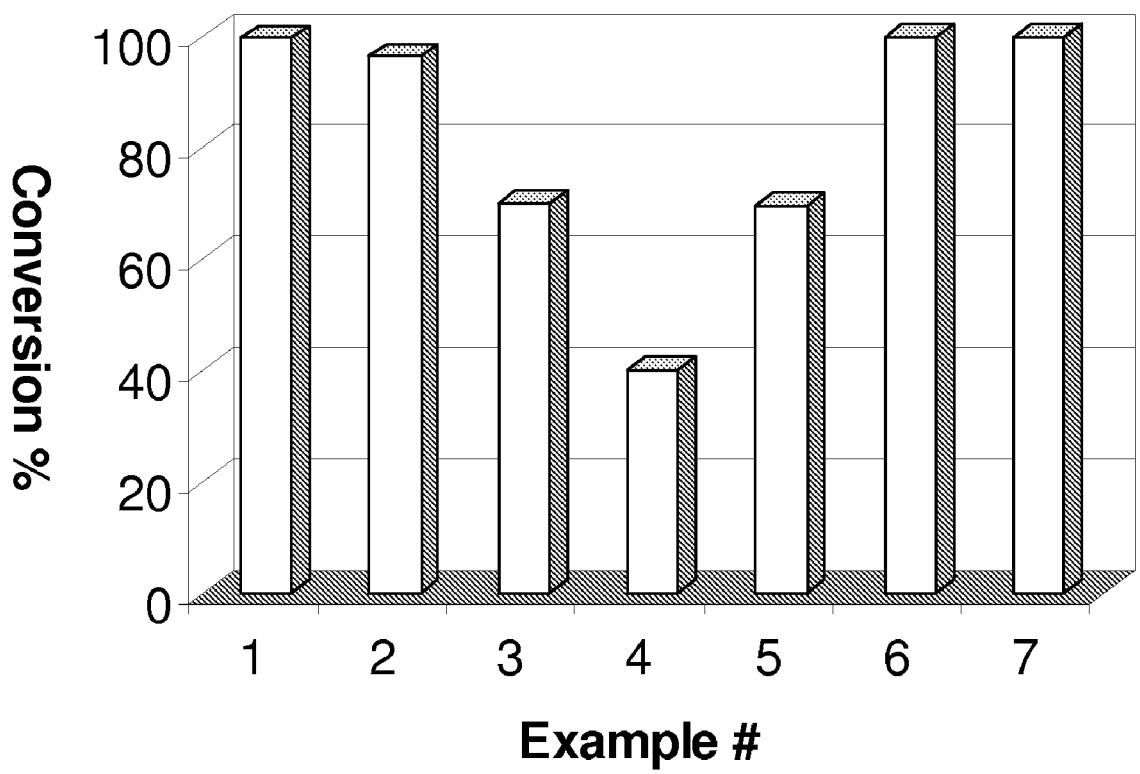
FIG. 1 is a graphical representation of the conversion levels achieved in examples 1 to 7.

The melt production of polycarbonate, or polycarbonate oligomers, using an ester-substituted diaryl carbonate results in several by-products including ester-substituted phenols. In order to achieve high plant efficiencies it is often desirable that such by-products be recycled to form, or reform, ester-substituted diaryl carbonates that are suitable for use, or reuse, in the melt production facility. This approach has the benefit of reducing the amount of by-product waste generated during polycarbonate production while streamlining and reducing costs incurred by melt polycarbonate production facilities. In order to achieve a high conversion of recycled ester-substituted phenols into ester-substituted diaryl carbonates, without the use of excessive amounts of phosgene, it has herein been found that the level of trialkyl amines and trialkyl phosphines, that have at least one methyl group, should be reduced in the recycle by-product ester-substituted phenol stream prior to the formation reaction of the ester-substituted diaryl carbonate.

The present invention may be understood more readily by reference to the following detailed description of preferred embodiments of the invention and the examples included therein. In the specification and the claims which follow, reference will be made to a number of terms which shall be defined to have the following meanings:

The singular forms "a", "an", and "the" include plural referents unless the context clearly dictates otherwise.

"Polycarbonate" refers to polycarbonates incorporating repeat units derived from at least one dihydroxy aromatic compound and includes copolyestercarbonates, for example a polycarbonate comprising repeat units derived from resorcinol, bisphenol A, and dodecandioic acid. Nothing in the description and claims of this application should be taken as limiting the polycarbonate to only one dihydroxy residue unless the context is expressly limiting. Thus, the application encompasses copolycarbonates with residues of 2, 3, 4, or more types of dihydroxy compounds.

"Selectivity" refers to the amount of ester-substituted phenol that is converted to product ester-substituted diaryl carbonate rather than to undesired byproducts. It is calculated as (mole ester-substituted phenol converted to mole ester-substituted diaryl carbonate/total mole of ester-substituted phenol consumed).

"Conversion" refers to the total amount of ester-substituted diaryl carbonate formed from the raw material ester-substituted phenol. It is calculated as 100−((weight ester-substituted phenol/(weight ester-substituted phenol+ester-substituted diaryl carbonate+weight by-products))*100).

"Catalyst degradation product" refers to the trialkyl (amine or phosphine) that may be produced from a reaction in which a trialkyl (ammonium or phosphonium) hydroxide is used as a catalyst. The trialkyl (ammonium or phosphonium) hydroxide used as a catalyst has a methyl group for at least one of its alkyl groups. The resulting trialkyl (amine or phosphine) catalyst degradation product will also have a methyl group for at least one of its alkyl groups.

Numerical values in the specification and claims of this application reflect average values. Furthermore, the numerical values should be understood to include numerical values which are the same when reduced to the same number of significant figures and numerical values which differ from the stated value by less than the experimental error of the measurement technique used in the present application to determine the value.

US patent application publication no. 2006/0025622, which is incorporated herein by reference, discusses several techniques used to produce ester-substituted diaryl carbonates from ester-substituted phenols. As disclosed in that publication, a preferred method of producing ester-substituted diaryl carbonates from ester-substituted phenols comprises the step of reacting ester-substituted phenol with phosgene in the presence of a tertiary amine catalyst, a phase transfer catalyst, or both. These catalysts have been found to accelerate the formation of ester-substituted diaryl carbonate product and to act to minimize the presence of the intermediate ester-substituted phenyl chloroformate in the product. Suitable phase transfer catalysts are widely available and include quaternary ammonium salts of aliphatic amines, quaternary ammonium salts of aromatic amines, quaternary phosphonium salts, sulfonium salts, polyethers and the like. The amount of phase transfer catalyst employed is typically in a range between 0.1 and 2 mole percent catalyst, and preferably between 0.25 and 1.0 mole percent catalyst per mole of ester-substituted phenol employed. In another embodiment of the present invention a tertiary amine is included as a catalyst for the formation of ester-substituted diaryl carbonates. The preferred tertiary amine used as a catalyst of the present invention is triethyl amine. The amount of the tertiary amine catalyst employed is typically in a range of between 0.01 and 1.00, for example between 0.01 and 0.09, mole percent catalyst based upon the number of moles of ester-substituted phenol employed in the reaction mixture.

Preferred processes for the formation of polycarbonate, or polycarbonate oligomers, using ester-substituted diaryl carbonates as a carbonate source are disclosed in US patent application publication Nos. 2005/0234211 and 2006/0069228 which are both incorporated by reference. In these disclosures it is explained that ester-substituted diaryl carbonates, such as BMSC, may be substituted for non-ester substituted diaryl carbonates, such as DPC, to increase polymerization reaction rates. Further, in these disclosures it is explained that it is often preferred that the reaction of the ester-substituted diaryl carbonate with a dihydroxy composition be catalyzed by a catalyst such as quaternary ammonium or quaternary phosphonium hydroxides. Such hydroxides serve to the promote the transesterification reaction between the carbonate source and the free hydroxyl ends of the dihydroxy compositions. For thermal stability, cost, and commercial availability reasons, inter alia, preferred examples of such compounds are tetramethyl ammonium hydroxide and tetramethyl phosphonium hydroxide. Upon the consumption of these preferred catalysts, in a reaction using the same, a catalyst degradation product comprising a trialkyl amine (e.g. trimethyl amine), a trialkyl phosphine (e.g. trimethyl phosphine), or both are produced.

Since the production of ester-substituted diaryl carbonates using ester-substituted phenols is preferably achieved in the presence of an ethyl amine or ethyl phosphine catalyst, for example triethyl amine or triethyl phosphine, it would be expected that a trialkyl amine, or trialkyl phosphine, degradation product of which at least one of the alkyl groups is a methyl group would aid in, or at least not hinder, the promotion of such a reaction. However, it has herein been found that trialkyl amine and trialkyl phosphine catalyst degradation products which have at least one of methyl group (e.g. trimethyl amine, dimethylethyl amine, diethylmethyl amine, trimethyl phosphine, dimethylethyl phosphine, and/or diethylmethyl phosphine), if present, in an ester-substituted phenol leads to poor conversion of such into ester-substituted diaryl carbonate, thereby requiring the use of excess phosgene to reach higher conversions.

In one embodiment the present invention provides an improved method of making an ester-substituted diaryl carbonate by reacting phosgene with a recycle stream of ester-substituted phenol from a reaction process using a tetraalkyl phosphonium hydroxide, a tetraalkyl ammonium hydroxide, or both, as a catalyst, the improvement comprising: treating the recycle stream to reduce a catalyst degradation product concentration, if catalyst degradation product is present, prior to the reaction with phosgene, wherein the catalyst degradation product comprises a trialkyl phosphine, a trialkyl amine, or both, and wherein at least one alkyl group of the tetraalkyl phosphonium hydroxide or the tetraalkyl ammonium hydroxide is a methyl group. In preferred embodiments the reaction of the recycle ester-substituted phenol stream with phosgene is carried out to a conversion of ester-substituted phenol into ester-substituted diaryl carbonate of greater than 80%, for example greater than 90%, more preferably greater than 95%, and most preferably greater than 98%.

The uses for the ester-substituted diaryl carbonate produced by the methods of the present invention are not particularly limited. In a preferred embodiment the ester-substituted diaryl carbonate will be used as a carbonate source in the melt production of polycarbonate as disclosed in the references cited above. For example, the present invention provides an improved method of making polycarbonate using a carbonate source comprising an ester-substituted diaryl carbonate prepared by reacting phosgene with a recycle stream of ester-substituted phenol from a reaction process using a tetraalkyl phosphonium hydroxide, tetraalkyl ammonium hydroxide, or both as a catalyst, the improvement comprises: treating the recycle stream to reduce catalyst degradation product concentration, if catalyst degradation product is present, prior to the reaction with phosgene. The catalyst degradation product comprises trialkyl phosphine, trialkyl amine, or both. At least one alkyl group of the tetraalkyl phosphonium hydroxide or tetraalkyl ammonium hydroxide is a methyl group.

The step of treating the recycle stream is performed regardless of whether catalyst degradation product is present, such that if it is present its concentration is reduced. In preferred embodiments the recycle ester-substituted phenol stream is analyzed to determine the concentration of the catalyst degradation product prior to treatment. For example, it is often the case that the amount of catalyst degradation product present in the recycle stream is greater than 1.00 ppm. In preferred embodiments of the present invention, the recycle stream is treated such that the catalyst degradation product present in the recycle stream after treatment is less than 1.00 ppm, more preferably less than 0.75 ppm, still more preferably less than 0.50 ppm, and most preferably less than 0.25 ppm. The means for reducing the concentration of the catalyst degradation product is not particularly limited as such may be accomplished by evaporation or distillation of the degradation product from the recycle stream. Since trialkyl amines and phosphines are soluble in water, it has been found to be preferred that the recycle stream be washed with water in a water extractor system. It has also been found that acid-scrubbing of the recycle ester-substituted phenol stream is a suitable method of extracting the catalyst degradation product. In a further embodiment, the concentration of the catalyst degradation product may be reduced by diluting the recycle stream with a stream of ester-substituted phenol containing less catalyst degradation product than the recycle stream, for example a stream of pure ester-substituted phenol.

The Process:

As detailed above, the present invention relates to the discovery that specific catalyst degradation products, if present in an ester-substituted phenol stream that is reacted with phosgene, hinder the formation of ester-substituted diaryl carbonates thereby requiring the use of excess phosgene to achieve high conversions. The concentration of the catalyst degradation product can be reduced by removing the degradation product from the ester-substituted phenol stream or by diluting the ester-substituted phenol stream with another ester-substituted phenol stream having a lower concentration of the catalyst degradation product prior to its reaction with phosgene to produce ester-substituted diaryl carbonate.

The recycle stream of ester-substituted phenol comes from a reaction process using tetraalkyl ammonium hydroxide, tetraalkyl phosphonium hydroxide, or both as catalysts wherein at least one of the alkyl groups of the tetraalkyl ammonium hydroxide or the tetraalkyl phosphonium hydroxide is a methyl group. The reaction from which the recycle stream comes is not particularly limited. For example, the recycle stream may come from a melt polymerization reaction producing polycarbonate or copolycarbonate oligomers or polymers or any other reaction that uses a tetraalkyl ammonium hydroxide or a tetraalkyl phosphonium hydroxide as a catalyst where at least one of the respective alkyl groups is a methyl group. When at least one of the alkyl groups of the tetraalkyl ammonium hydroxide or the tetraalkyl phosphonium hydroxide is a methyl group, their degradation products (i.e. trialkyl amine or trialkyl phosphine) may have a methyl alkyl group. As stated above, these trialkyl amines or trialkyl phosphines that have at least one methyl group have been found to hinder the formation reaction of the ester-substituted diaryl carbonate.

In a preferred example, the recycle ester-substituted phenol stream comes from a polycarbonate melt production facility using tetramethyl ammonium hydroxide or tetramethyl phosphonium hydroxide as a catalyst to affect the reaction of the free-hydroxyl ends of dihydroxy compounds with an ester-substituted diaryl carbonate as a carbonate source.

The Ester-Substituted Diaryl Carbonate:

In one aspect of the present invention a method is provided for the preparation of ester-substituted diaryl carbonates having structure I from a recycle stream of ester-substituted phenols having structure II,

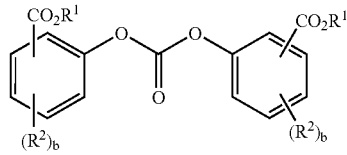

wherein $R^1$ is independently at each occurrence a $C_1$-$C_{20}$ alkyl radical, $C_4$-$C_{20}$ cycloalkyl radical, or $C_4$-$C_{20}$ aromatic radical; $R^2$ is independently at each occurrence a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and b is independently at each occurrence an integer 0-4.

Examples of ester-substituted diaryl carbonates which may be prepared using the method of the present invention include bis-methyl salicyl carbonate (i.e. BMSC) (CAS Registry No. 82091-12-1), bis-ethyl salicyl carbonate, bis-propyl salicyl carbonate, bis-butyl salicyl carbonate, bis-benzyl salicyl carbonate, bis-methyl 4-chlorosalicyl carbonate and the like. Typically bis-methyl salicyl carbonate is preferred for use in melt polycarbonate synthesis due to its lower molecular weight and higher vapor pressure.

The Ester-Substituted Phenol:

The recycle stream of ester-substituted phenol used in accordance with the present invention comprises at least one compound selected from among phenols having structure II,

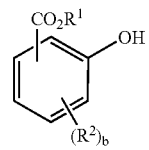

wherein $R^1$, $R^2$, and b are defined as in structure I.

Examples of ester-substituted phenols which may serve as starting materials for the method of the present invention include phenyl salicylate, methyl salicylate (i.e. MS), ethyl salicylate, propyl salicylate, butyl salicylate, benzyl salicylate, methyl 4-chloro salicylate and the like. Typically, MS is a by-product of transesterification reactions using BMSC. Further, MS is the preferred ester-substituted phenol used in the preparation of BMSC as described in the patents cited above. Further, recycled MS may be used to form BMSC according to the present invention.

Reaction Catalysts and their Degradation Products:

As detailed above preferred polymerization catalysts used in the melt production of polycarbonate include tetraalkyl ammonium hydroxides and tetraalkyl phosphonium hydroxides having structure III,

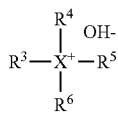

wherein $R^3$-$R^6$ represent alkyl groups having from 1 to 30, for example 1 to 4, carbon atoms in length; at least one of the $R^3$-$R^6$ groups is a —($CH_3$) group; and X+ represents phosphorus or nitrogen.

Suitable and non-limiting examples of tetraalkyl ammonium hydroxides and tetraalkyl phosphonium hydroxides having structure III are tetramethyl phosphonium hydroxide, diethyldimethyl phosphonium hydroxide, tetramethyl ammonium hydroxide, and diethyldimethyl ammonium hydroxide.

As a reaction proceeds, using a catalyst of structure III, a catalyst degradation product may be formed. The catalyst degradation product, depending on the selected catalyst will have structure IV,

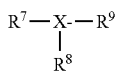

wherein $R^7$-$R^9$ represent alkyl groups having from 1 to 30, for example 1 to 4, carbon atoms in length; and X− represents phosphorus or nitrogen. When the catalyst having structure III has one —($CH_3$) group, one of the $R^7$-$R^9$ groups may be a —($CH_3$) group. when the catalyst having structure III has at least two —($CH_3$) groups, at least one of the $R^7$-$R^9$ groups will be a —($CH_3$) group. For example when the catalyst having structure III is tetramethyl ammonium hydroxide, the catalyst degradation product, if present, comprises trimethyl amine. If the catalyst having structure IV is tetramethyl phosphonium hydroxide, the catalyst degradation product, if present, comprises trimethyl phosphine. If both a tetramethyl (phosphonium and ammonium) hydroxide are used as catalysts, both a trimethyl (phosphine and amine) may be present in the catalyst degradation product.

In another embodiment where the catalyst having structure III is diethyldimethyl phosphonium hydroxide, the catalyst degradation product, if present, comprises diethylmethyl phosphine, ethyldimethyl phosphine, or a combination thereof. In yet a further embodiment where the catalyst having structure III is a diethyldimethyl ammonium hydroxide, the catalyst degradation product, if present, comprises diethylmethyl amine, ethyldimethyl amine, or a combination thereof.

Figure 2:
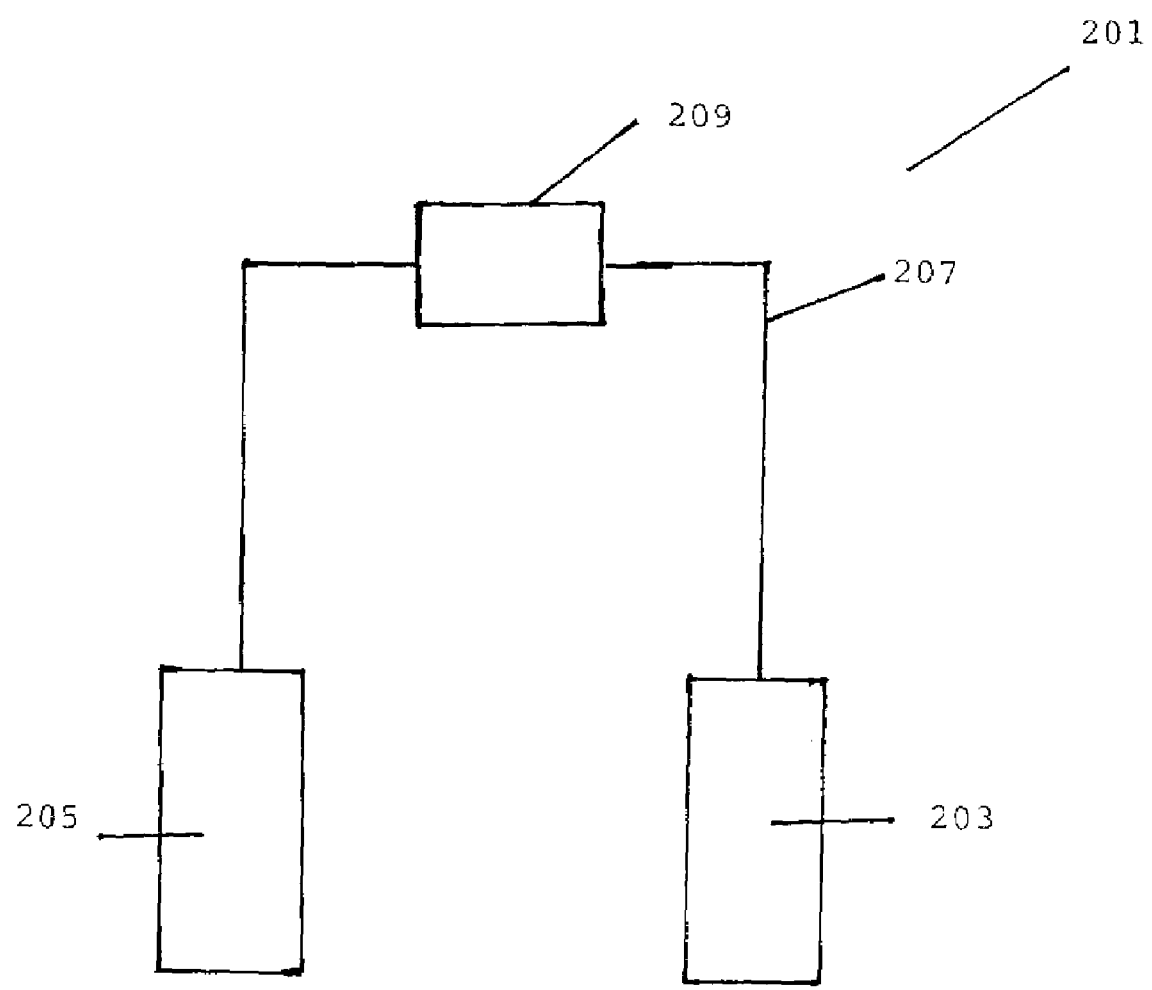
FIG. 2 is a block diagram showing an embodiment of the present invention.

The Facility:

As detailed in FIG. 2, in another embodiment, the present invention provides a facility for making polycarbonate. The facility 201 comprises (i) a melt polymerization reactor system 203, (ii) an ester-substituted diaryl carbonate reactor system 205, (iii) a recycle ester-substituted phenol line 207, and (iv) means 209 for reducing catalyst degradation product concentration in the recycle ester-substituted phenol line.

The (i) melt polymerization reactor system 203 comprises a reaction vessel containing a reaction mixture comprising a dihydroxy compound, an ester-substituted diaryl carbonate, and a catalyst. The catalyst comprises a tetraalkyl ammonium hydroxide, a tetraalkyl phosphonium hydroxide, or both, where at least one of the alkyl groups is a methyl group. The melt polymerization reactor system may be as described above in the cited and incorporated patent application publication. For example the reactor system, the reaction conditions, and the components of reaction mixture are preferably those as disclosed in the cited references.

The (ii) ester-substituted diaryl carbonate reactor system 205 comprises a reaction vessel containing an ester-substituted phenol and phosgene. The ester-substituted diaryl carbonate reactor system is not particularly limited and is preferably that as described in U.S. patent application Ser. No. 10/984,318 as cited and incorporated by reference above.

The (iii) recycle ester-substituted phenol line 207 is connected to both the melt polymerization reactor system 203 and to the ester-substituted diaryl carbonate reactor system 205. The recycle line 207 contains the recycle stream of an ester-substituted phenol and a catalyst degradation product, wherein the catalyst degradation product comprises a trialkyl amine, a trialkyl phosphine, or both.

The (iv) means 209 for reducing catalyst degradation product concentration in the recycle ester-substituted phenol line 207 is connected to the recycle line 207 between the melt polymerization reactor system 203 and the ester-substituted diaryl carbonate reactor system 205. In exemplary embodiments means 209 removes the catalyst degradation product from the recycle line 207. For example means 209 may be an aqueous extraction tower containing water or acid, an evaporator, a distillation column, or any combination thereof disposed on the recycle line. In another embodiment means 209 serves to reduce the concentration of the catalyst degradation product in the recycle line by diluting the recycle stream another ester-substituted phenol stream having a lower concentration of the catalyst degradation product. In this embodiment means 209 contains a mixing tank along with a clean ester-substituted phenol line.

Figure 3:
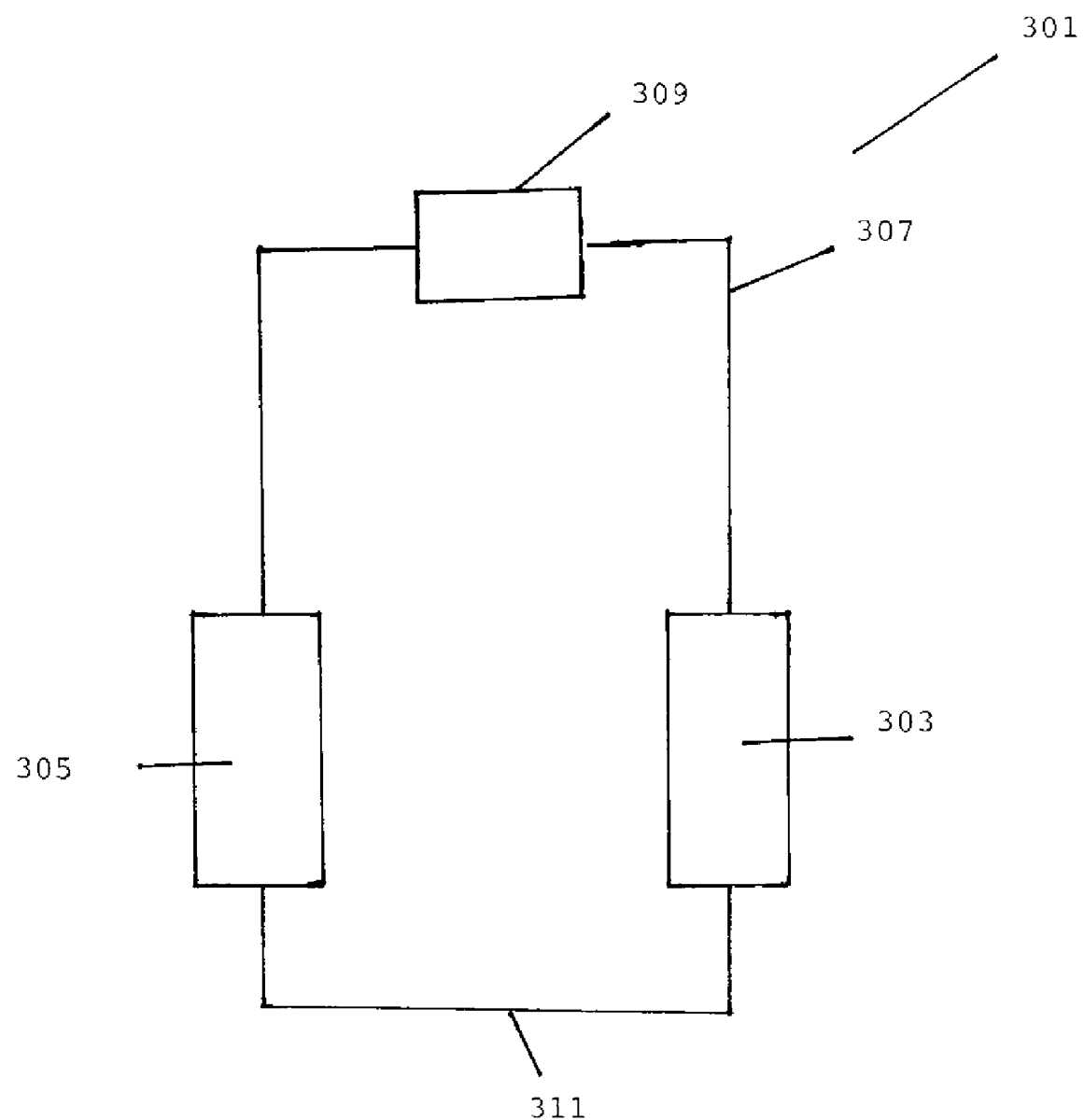
FIG. 3 is a block diagram showing an embodiment of the present invention.

As depicted in FIG. 3, in another embodiment the facility 301 further comprises an ester-substituted diaryl carbonate line 311, in addition to the (i) melt polymerization reactor system 303, (ii) an ester-substituted diaryl carbonate reactor system 305, (iii) recycle ester-substituted phenol line 307, and (iv) means 309 for reducing catalyst degradation product concentration in the recycle ester-substituted phenol line 309 as described above. The ester-substituted diaryl carbonate line 311 connects the ester-substituted diaryl carbonate reactor system 305 with the melt polymerization reactor system 303. The ester-substituted diaryl carbonate line 311 contains ester-substituted diaryl carbonate formed in the (ii) ester-substituted diaryl carbonate reactor system 305 using the recycle ester-substituted phenol contained in recycle line 307.

EXAMPLES

Having described the invention in detail, the following examples are provided. The examples should not be considered as limiting the scope of the invention, but merely as illustrative and representative thereof.

Equipment:

A 2-liter glass reactor was fitted with twin 6-blade impellers, a recirculation loop, a reflux condenser, and ports for adding phosgene and NaOH solution. A pH electrode was mounted in the recirculation loop.

Example 1

MS

The reactor was charged with 470 ml of methylene chloride, 246 g of methyl salicylate (1.62 moles) and 0.062 g of triethylamine (0.000614 moles). Phosgene (112 g, 1.13 moles) was added at a rate of 4.0 g/min for 28 minutes. 22% sodium hydroxide was added at a rate of 16.9 g/min until about 370 g had been added, then added at a variable rate sufficient to maintain a pH of about 12. After the addition of about 94 g of phosgene, an additional amount of triethylamine (1.6 g, 0.016 mole) was added. Color of the agitated reaction mixture was white throughout the reaction.

Example 2

MS Spiked with 0.25 ppm TMA

The reactor was charged with 470 ml of methylene chloride, 246 g of methyl salicylate (1.62 moles), 0.062 g of triethylamine (0.000614 moles) and 53 microliters of a 0.125% aqueous solution of trimethylamine. Phosgene (112 g, 1.13 moles) was added at a rate of 4.0 g/min for 28 minutes. 22% sodium hydroxide was added at a rate of 16.9 g/min until about 260 g had been added, then added at a variable rate sufficient to maintain a pH of about 11.5. After the addition of about 94 g of phosgene, an additional amount of triethylamine (1.6 g, 0.016 mole) was added.

Example 3

MS Spiked with 1 ppm TMA

The reactor was charged with 470 ml of methylene chloride, 246 g of methyl salicylate (1.62 moles), 0.062 g of triethylamine (0.000614 moles) and 1.1 microliters of a 25% aqueous solution of trimethylamine. Phosgene (112 g, 1.13 moles) was added at a rate of 4.0 g/min for 28 minutes. 22% sodium hydroxide was added at a rate of 16.9 g/min until about 415 g had been added, then added at a variable rate sufficient to maintain a pH of about 12. After the addition of about 94 g of phosgene, an additional amount of triethylamine (1.6 g, 0.016 mole) was added.

Example 4

MS Spiked with 5 ppm TMA

The reactor was charged with 470 ml of methylene chloride, 246 g of methyl salicylate (1.62 moles), 0.062 g of triethylamine (0.000614 moles) and 5.3 microliters of a 25% aqueous solution of trimethylamine. Phosgene (112 g, 1.13 moles) was added at a rate of 4.0 g/min for 28 minutes. 22% sodium hydroxide was added at a rate of 16.9 g/min until about 415 g had been added, then added at a variable rate sufficient to maintain a pH of about 12. After the addition of about 94 g of phosgene, an additional amount of triethylamine (1.6 g, 0.016 mole) was added.

Results Examples 1-4

The result of examples 1-4 are depicted in Table 1 below which shows a correlation between the presence of TMA and the conversion of MS to BMSC. The conversion of MS into BMSC decreases with an increase of the TMA catalyst degradation product.

Example 5

Recycled MS with 1 ppm TMA or Less

The reactor was charged with 470 ml of methylene chloride, 246 g of recycled methyl salicylate (1.62 moles) (recycled from oligomerizer overhead, using TMAH as a catalyst, containing about 1 ppm TMA based on MS mass as determined by GC-MS), 0.062 g of triethylamine (0.000614 moles). Phosgene (112 g, 1.13 moles) was added at a rate of 4.0 g/min for 28 minutes. 22% sodium hydroxide was added at a rate of 16.9 g/min until about 430 g had been added, then added at a variable rate sufficient to maintain a pH of about 12. After the addition of about 94 g of phosgene, an additional amount of triethylamine (1.6 g, 0.016 mole) was added.

Results Example 5

Example 5 demonstrates that an unpurified recycle stream of MS from a reaction process using tetramethyl ammonium hydroxide as a catalyst may contain TMA catalyst degradation product. Here the product is present in the amount of about 1 ppm in the recycle MS. The conversion results of Example 5 compare with Example 3, which has a similar amount of TMA, in that after the addition of 1.13 moles of phosgene conversions of around 70% are achieved.

Example 6

Aqueous HCl Extracted Recycle MS

The reactor was charged with 470 ml of methylene chloride, 246 g of recycled methyl salicylate (1.62 moles) (recycled from oligomerizer overhead, using TMAH as a catalyst, and washed with an equal volume of 1N HCl, then separated from the acid solution in a separatory funnel) containing less than 1 ppm TMA based on MS mass analyzed by GC-MS), 0.062 g of triethylamine (0.000614 moles). Phosgene (112 g, 1.13 moles) was added at a rate of 4.0 g/min for 28 minutes. 22% sodium hydroxide was added at a rate of 16.9 g/min until about 404 g had been added, then added at a variable rate sufficient to maintain a pH of about 12. After the addition of about 94 g of phosgene, an additional amount of triethylamine (1.6 g, 0.016 mole) was added.

Example 7

Water Extracted Recycle MS

The reactor was charged with 470 ml of methylene chloride, 246 g of recycled methyl salicylate (1.62 moles) (recycled from oligomerizer overhead, using TMAH as a catalyst, and washed with an equal volume of deionized water, then separated from the aqueous solution in a separatory funnel) containing less than 1 ppm TMA based on MS mass analyzed by GC-MS), 0.062 g of triethylamine (0.000614 moles). Phosgene (112 g, 1.13 moles) was added at a rate of 4.0 g/min for 28 minutes. 22% sodium hydroxide was added at a rate of 16.9 g/min until about 426 g had been added, then added at a variable rate sufficient to maintain a pH of about 12. After the addition of about 94 g of phosgene, an additional amount of triethylamine (1.6 g, 0.016 mole) was added.

Results Examples 6 & 7

The recycle MS stream of example 5 washed with an acid in example 6 and with water in example 7 to extract the catalyst degradation product TMA from the stream prior to its reaction with phosgene. In these examples, the TMA was extracted to levels of less than 1 ppm in the MS stream. After the extraction of the TMA, the MS stream was reacted with phosgene and conversions of over 99% were achieved similar to that of pure MS of example 1. Examples 6 and 7 further demonstrate that desirability of extracting the catalyst degradation product from the recycle MS stream prior to the BMSC formation reaction.

TABLE 1

Results of Examples 1-7

| Example | % Conv | % Selectivity | % MS | % BMSC | % Trimer | TMA ppm |
|---|---|---|---|---|---|---|
| 1 | 99.72 | 99.45 | 0.28 | 99.14 | 0.29 | 0 |
| 2 | 96.44 | 99.21 | 3.56 | 95.65 | 0.37 | 0.25 |
| 3 | 70.11 | 99.73 | 29.89 | 69.89 | 0.06 | 1 |
| 4 | 40.13 | 99.81 | 59.87 | 40.04 | 0.04 | 5 |
| 5 | 69.72 | 99.38 | 30.28 | 69.27 | 0.15 | about 1 |
| 6 | 99.8 | 99.24 | 0.2 | 98.95 | 0.42 | less than 1 |
| 7 | 99.82 | 99.26 | 0.18 | 98.99 | 0.31 | less than 1 |

The invention claimed is:

1. In a method of making an ester-substituted diaryl carbonate by reacting phosgene with a recycle stream of ester-substituted phenol from a reaction process using a tetraalkyl phosphonium hydroxide, a tetraalkyl ammonium hydroxide, or both, as a catalyst, the improvement comprising:
treating the recycle stream to reduce a catalyst degradation product concentration, if catalyst degradation product is present, prior to the reaction with phosgene,
wherein the catalyst degradation product comprises a trialkyl phosphine, a trialkyl amine, or both, and
wherein at least one alkyl group of the tetraalkyl phosphonium hydroxide or the tetraalkyl ammonium hydroxide is a methyl group.

2. The improvement of claim 1, wherein catalyst degradation product is initially present and is reduced to a concentration of less than 1.00 ppm in the recycle stream.

3. The improvement of claim 1, wherein reducing catalyst degradation product concentration in the recycle stream is accomplished by washing the recycle stream with an aqueous solution.

4. The improvement of claim 3, wherein the aqueous solution is water.

5. The improvement of claim 3, wherein the aqueous solution is acidic.

6. The improvement of claim 1, wherein reducing catalyst degradation product concentration in the recycle stream is accomplished by mixing the recycle stream with an ester-substituted phenol stream containing a lower concentration of the catalyst degradation product than the recycle stream.

7. The improvement of claim 1, wherein:
the tetraalkyl phosphonium hydroxide comprises tetramethyl phosphonium hydroxide, diethyldimethyl phosphonium hydroxide, or both, and
the tetraalkyl ammonium hydroxide comprises tetramethyl ammonium hydroxide, diethyldimethyl ammonium hydroxide, or both.

8. The improvement of claim 1, wherein the catalyst degradation product is trimethyl phosphine, diethylmethyl phosphine, dimethylethyl phosphine, trimethyl amine, diethylmethyl amine, dimethylethyl amine, or any combination thereof.

9. In a method of making a polycarbonate using a carbonate source comprising an ester-substituted diaryl carbonate prepared by reacting phosgene with a recycle stream of ester-substituted phenol from a reaction process using a tetraalkyl phosphonium hydroxide, a tetraalkyl ammonium hydroxide, or both, as a catalyst the improvement comprising:
treating the recycle stream to reduce a catalyst degradation product concentration, if catalyst degradation product is present, prior to the reaction with phosgene,
wherein the catalyst degradation product comprises a trialkyl phosphine, a trialkyl amine, or both, and
wherein at least one alkyl group of the tetraalkyl phosphonium hydroxide or the tetraalkyl ammonium hydroxide is a methyl group.

10. The improvement of claim 9, wherein the catalyst degradation product is present and is reduced to a concentration of less than 1.00 ppm in the recycle stream.

11. The improvement of claim 9, wherein reducing the catalyst degradation product concentration in the recycle stream is accomplished by washing the recycle stream with an aqueous solution.

12. The improvement of claim 11, wherein the aqueous solution is water.

13. The improvement of claim 11, wherein the aqueous solution is acidic.

14. The improvement of claim 9, wherein reducing the catalyst degradation product concentration in the recycle stream is accomplished by mixing the recycle stream with an ester-substituted phenol stream containing a lower concentration of catalyst degradation product than the recycle stream.

15. The improvement of claim 9, wherein:
the tetraalkyl phosphonium hydroxide comprises tetramethyl phosphonium hydroxide, diethyldimethyl phosphonium hydroxide, or both, and
the tetraalkyl ammonium hydroxide comprises tetramethyl ammonium hydroxide, diethyldimethyl ammonium hydroxide, or both.

16. The improvement of claim 9, wherein the catalyst degradation product is trimethyl phosphine, diethylmethyl phosphine, dimethylethyl phosphine, trimethyl amine, diethylmethyl amine, dimethylethyl amine, or any combination thereof.

17. A facility for making polycarbonate comprising:
(i) a melt polymerization reactor system comprising a reaction vessel containing a reaction mixture, said reaction mixture comprising a dihydroxy compound, an ester-substituted diaryl carbonate, and a catalyst, wherein the catalyst comprises a tetraalkyl ammonium hydroxide, a tetraalkyl phosphonium hydroxide, or both,
wherein at least one alkyl group of the tetraalkyl phosphonium hydroxide or the tetraalkyl ammonium hydroxide is a methyl group,
(ii) an ester-substituted diaryl carbonate reactor system comprising a reaction vessel containing an ester-substituted phenol and phosgene,
(iii) a recycle ester-substituted phenol line, connected to both the melt polymerization reactor system and to the ester-substituted diaryl carbonate reactor system, the recycle line containing a recycle stream of an ester-substituted phenol and a catalyst degradation product, wherein the catalyst degradation product comprises a trialkyl amine, a trialkyl phosphine, or both, and (iv) an aqueous extraction tower for reducing catalyst degradation product concentration in the recycle ester-substituted phenol line, connected to the recycle ester-substituted phenol line between the melt polymerization reactor system to the ester-substituted diaryl carbonate reactor system.

18. The facility of claim 17, further comprising:
(v) an ester-substituted diaryl carbonate line, connected to both the melt polymerization reactor and to the ester-substituted diaryl carbonate reactor system, the ester-substituted diaryl carbonate line containing an ester-substituted diaryl carbonate formed in the ester-substituted diaryl carbonate reactor system.

19. A facility for making polycarbonate comprising:
(i) a melt polymerization reactor system comprising a reaction vessel containing a reaction mixture, said reaction mixture comprising a dihydroxy compound, an ester-substituted diaryl carbonate, and a catalyst, wherein the catalyst comprises a tetraalkyl ammonium hydroxide, a tetraalkyl phosphonium hydroxide, or both,
wherein at least one alkyl group of the tetraalkyl phosphonium hydroxide or the tetraalkyl ammonium hydroxide is a methyl group,
(ii) an ester-substituted diaryl carbonate reactor system comprising a reaction vessel containing an ester-substituted phenol and phosgene,
(iii) a recycle ester-substituted phenol line, connected to both the melt polymerization reactor system and to the ester-substituted diaryl carbonate reactor system, the recycle line containing a recycle stream of an ester-substituted phenol and a catalyst degradation product, wherein the catalyst degradation product comprises a trialkyl amine, a trialkyl phosphine, or both, and
(iv) a distillation column for reducing catalyst degradation product concentration in the recycle ester-substituted phenol line, connected to the recycle ester-substituted phenol line between the melt polymerization reactor system to the ester-substituted diaryl carbonate reactor system.

20. The facility of claim 19, further comprising:
(v) an ester-substituted diaryl carbonate line, connected to both the melt polymerization reactor and to the ester-substituted diaryl carbonate reactor system, the ester-substituted diaryl carbonate line containing an ester-substituted diaryl carbonate formed in the ester-substituted diaryl carbonate reactor system.

21. The improvement of claim 1, wherein the recycle stream of ester-substituted phenol comes from a melt polymerization reaction that produces polycarbonate.

22. The improvement of claim 9, wherein the recycle stream of ester-substituted phenol comes from a melt polymerization reaction that produces polycarbonate.

* * * * *